United States Patent [19]

Wee

[11] Patent Number: 5,076,832
[45] Date of Patent: Dec. 31, 1991

[54] CERTAIN 3-(SUBSTITUTED PHENYL)-5-(SUBSTITUTED PHENYL)-1-ETHYLIMIDAZOLIDINE-4-ONES AS HERBICIDES

[75] Inventor: Siok H. H. Wee, Berkeley, Calif.
[73] Assignee: ICI Americas Inc., Willington, Del.
[21] Appl. No.: 556,236
[22] Filed: Jul. 20, 1990
[51] Int. Cl.$^5$ .................. A01N 43/50; C07D 233/70
[52] U.S. Cl. ........................................... 71/92; 548/301
[58] Field of Search .................. 514/386; 548/301; 71/92

[56] References Cited

U.S. PATENT DOCUMENTS 4,614,535  9/1986  Schmierer .......................... 71/92

FOREIGN PATENT DOCUMENTS 143973  11/1980  Japan .

OTHER PUBLICATIONS

Chem Abstracts 068-095818 of French Patent 1480090 5/5/67.

Primary Examiner—Mary C. Lee
Assistant Examiner—Peter Davis

[57] ABSTRACT

Compounds having the formula

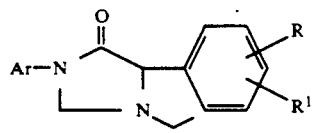

wherein R and $R^1$ are hydrogen, halogen, trifluoromethyl or $C_1$-$C_4$ alkoxy and Ar is a substituted phenyl group as herbicide.

24 Claims, No Drawings

CERTAIN 3-(SUBSTITUTED PHENYL)-5-(SUBSTITUTED PHENYL)-1-ETHYLIMIDAZOLIDINE-4-ONES AS HERBICIDES

BACKGROUND OF THE INVENTION

U.S Pat. No. 4,891,058 relates to certain herbicidal 1-alkyl-3- aryl imidazolidine -2,4-diones that have the structural formula

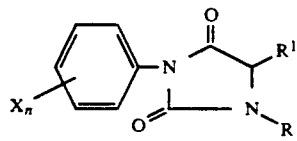

wherein R is lower alkyl, $R^1$ is phenyl or substituted phenyl, X is alkyl, halo, haloalkyl or combinations thereof and N is the integer 0, 1, 2 or 3.

DESCRIPTION OF THE INVENTION

This invention relates to 3-substituted-phenyl-5-(substituted or unsubstituted phenyl)-1-ethyl imidazolidine-4-one compounds and their use as herbicides.

One embodiment of this invention is an herbicidal composition comprising an herbicidally active 3-substituted phenyl-5-(substituted or unsubstituted phenyl)-1-ethyl imidazolidine-4-one and an inert carrier therefor. The substituents on the two phenyl moieties are preferably substituted with groups hereinafter defined.

Also, embodied within the scope of this invention are novel compounds having the following structural formula

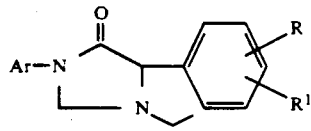

wherein

R is hydrogen; halogen, preferably fluorine; trifluoromethyl or $C_1$–$C_4$ alkoxy preferably, methoxy, most preferably fluorine or trifluoromethyl, $R_1$ is hydrogen; halogen, preferably fluorine; trifluoromethyl or $C_1$–$C_4$ alkoxy, preferably methoxy, most preferably fluorine;

Ar is the group

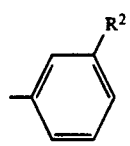

wherein $R^2$ is trifluoromethyl or halogen, preferably fluorine or the group

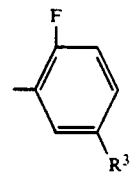

wherein $R^3$ is hydrogen, fluorine or trifluoromethyl, preferably trifluoromethyl.

The term "$C_1$–$C_4$ alkoxy" includes methoxy, ethoxy, n-propoxy, isopropoxy, and the four butoxys. The term "halogen" includes chlorine, bromine, iodine and fluorine.

The compounds of this invention are active herbicides of a general type. That is, they are herbicidally effective against a wide range of plant species. The method of controlling undesirable vegetation of the present invention comprises applying an herbicidally effective amount of the above-described compound to the area where control is desired.

The compounds of the present can be prepared by the following multi-step general method.

The imidazolidine-4-ones of this invention are prepared from the cyclization of N-aryl-2-(substituted phenyl)-2-ethylaminoacetamides using paraformaldehyde as the source of the methylene unit in the 2-position of the 5-membered imidazolidine ring. The reaction requires one equivalent of paraformaldehyde and one equivalent of a base such as potassium carbonate in a solvent such ethanol with heating to refluxing. The reaction scheme is as follows:

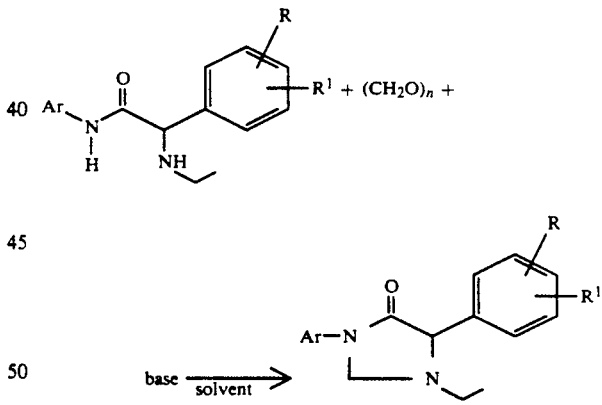

The preparation of the intermediate, N-aryl-2-(substituted phenyl)-2-ethylaminoacetamide is described in U.S. Pat. No. 4,891,058. The synthesis of this intermediate involves the displacement of the corresponding 2-chloroacetamide with aqueous ethylamine in a solvent such as ethanol at ambient temperature according to the following reaction scheme:

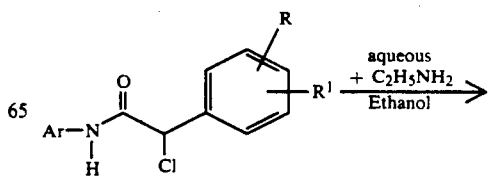

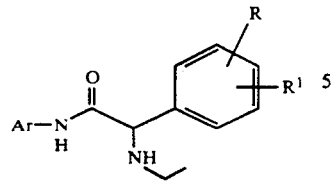

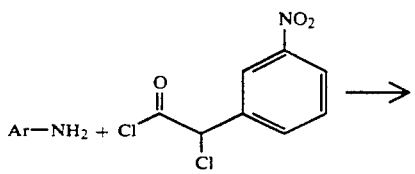

The method for the preparation of the N-aryl-2-(substituted phenyl)-2-chloroacetamides depends on the substitution on the 2-phenyl ring. When R and R¹ are hydrogen then the requisite aniline is reacted with 2-chloro-2-phenylacetyl chloride in the presence of a base such as triethylamine in a solvent such as methylene chloride as 0° C. to ambient temperature to provide the desired 2-chloroacetamide derivative according to the following reaction scheme:

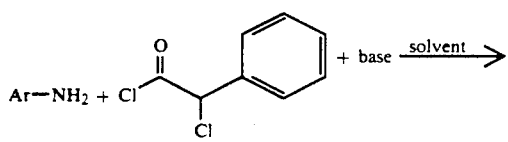

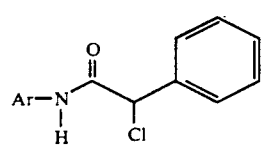

When R is a 3-nitro group and R¹ is hydrogen, the desired 2-chloro-2-(3-nitrophenyl)acetyl chloride is obtained from the nitration of 2-chloro-2-phenylacetyl chloride using sulfuric acid and fuming nitric acid. This reaction results in nitration of the phenyl ring at the 3-position and the partial hydrolysis of the acid chloride to the corresponding acetic acid. The reaction mixture is treated with oxalyl chloride and a catalytic amount of N,N-dimethylformamide to give the desired 2-chloro-2-(3-nitrophenyl)acetyl chloride according to the following reaction scheme:

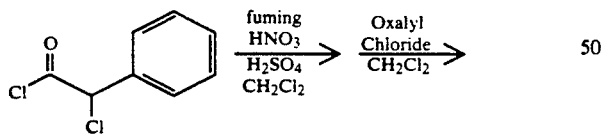

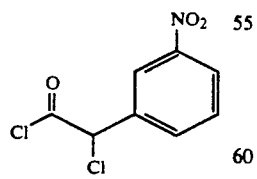

The 2-chloro-2-(3-nitrophenyl)acetyl chloride can be reacted with an equilmolar amount of the requisite aniline in a solvent such as methylene chloride with an equilmolar amount of a base such as triethylamine with recovery by conventional techniques according to the following reaction:

For all the other 2-(substituted phenyl) derivatives, the N-aryl-2-chloro-2-(substituted phenyl)acetamides are prepared based on the method described in H. G. Cook and E. K. Fields, *J. Org. Chem* 1961. 27. 3686. The three-step reaction scheme is done by first reacting the requisite aniline with the desired substituted benzaldehyde in an inert solvent such as toluene to give an imine. In the second step, the imine is converted to the dichloroaziridine by reacting it with dichlorocarbene which is generated in situ from chloroform and a base such as sodium hydroxide. In the third step the desired 2-chloroacetamide is prepared by the hydrolysis of the reaction product of the second step.

The three reactions are as follows:

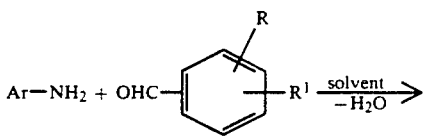

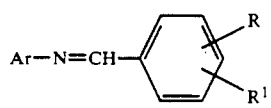

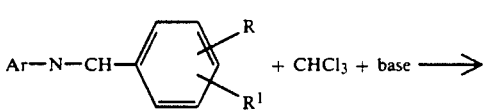

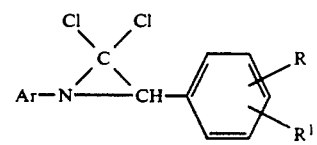

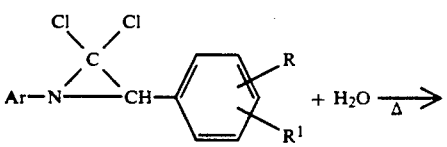

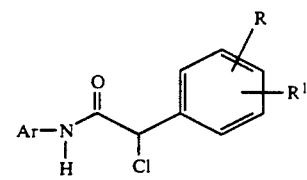

The following examples teach the synthesis of representative compounds and intermediates.

EXAMPLE I

N-(3-trifluoromethylphenyl)-2-chloro-2-phenylacetamide

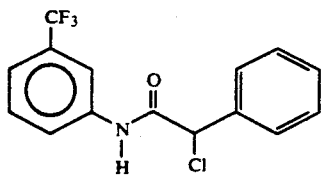

A toluene [350 milliliters (mL)] solution of 3-aminobenzotrifluoride [35.5 grams (g) 0.22 mol] and pyridine (19.1 grams, 0.24 mol) was cooled in an ice bath. 2-Chloro-2-phenylacetyl chloride (45.8 grams, 0.24 mol) was added dropwise. The mixture was allowed to warm to room temperature and stirred overnight. The reaction mixture was diluted with ethyl acetate (100 mL) and washed with water (2 ×200 mL) and dried with magnesium sulfate. The solvent was removed in a rotary evaporator to provide the desired N-(3-trifluoromethylphenyl)-2-chloro-2-phenylacetamide (61.6 grams, 89% yield) whose structure was confirmed by nuclear magnetic resonance, infra-red spectroscopy, and mass spectroscopy analysis.

EXAMPLE II

N-(3-trifluoromethylphenyl)-2-ethylamino-2phenylacetamide

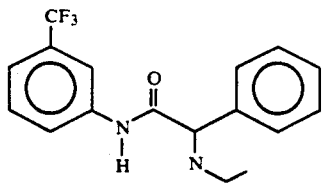

An ethanolic (200 mL) solution of N-(3-trifluoromethylphenyl)-2-chloro-2-phenylacetamide (200.0 grams, 0.06 mol) and 70% aqueous ethylamine (75 mL, excess) and potassium iodide (1.0 gram, catalytic) was stirred at room temperature. The reaction was followed by thin layer chromatography (3:1 hexane-ethyl acetate). The mixture was worked up by removing the ethanol and the excess ethyl amine in a rotary evaporator. The residue was redissolved in fresh ethanol and concentrated hydrochloric acid (excess) was added to convert the product to its hydrochloride salt. Water and other excess reagents were removed by azeotropic distillation in a rotary evaporator. The salt was washed with ethyl ether and dissolved in saturated sodium bicarbonte to regenerate the amine. The product was extracted into ethyl acetate and isolated to give the desired N-(3-trifluoromethylphenyl)-2-ethylamino-2-phenylacetamide (17.1 grams, 89% yield) whose structure was confirmed by nuclear magnetic resonance, infra-red spectroscopy, and mass spectroscopy analysis.

EXAMPLE III

1-Ethyl-5-phenyl-3-(3-trifluoromethylphenyl) imidazolidine-4one

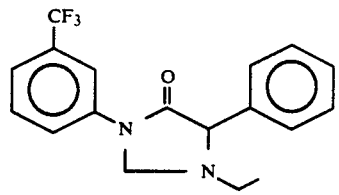

An ethanolic (50 mL) solution of the above N-aryl-2-ethylamino-2-phenylacetamide prepared in Example II (6.8 grams, 0.02 mol) and paraformaldehyde (0.65 grams, 0.02 mol) and potassium carbonate (1.5 grams, 0.01 mol) was heated under reflux for 2 hours. The reaction was followed by thin layer chromatography (3:1 hexane-ethyl acetate). The mixture was concentrated in a rotary evaporator. The product was extracted into ethyl acetate and washed with water and isolated to give the desired 1-ethyl-5-phenyl-3-(3-trifluoromethylphenyl) imidazolidine-4-one (6.8 grams, 97% yield) whose structure was confirmed by nuclear magnetic resonance, infra-red spectroscopy, and mass spectroscopy analysis.

EXAMPLE IV

2-Chloro-2-(3-nitrophenyl)acetyl chloride

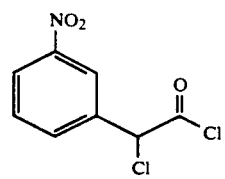

To a methylene chloride (i000 mL) solution of 2-chloro-2-phenylacetyl chloride (50.0 grams, 0.26 mol) and concentrated sulfuric acid (100 mL) cooled in an ice bath was added dropwise fuming nitric acid (20.0 grams, 0.32 mol). The mixture was allowed to stir for two hours and then poured into ice (500 mL). The organic layer was washed with saturated sodium chloride solution (2×200 mL), dried with magnesium sulfate and filtered through a thin pad of silica gel. To this methylene chloride solution was added oxalyl chloride (13.2 grams, 0.52 mol) and N,N-dimethylformamide (9 drops). The mixture was stirred at room temperature for 1.5 hours, was heated under reflux for 20 minutes, and concentrated in a rotary evaporator to give the desired 2-chloro-2-(3-nitrophenyl)acetyl chloride (50.2 grams, 81% yield whose structure was confirmed by nuclear magnetic resonance, infra-red spectroscopy, and mass spectroscopy analysis.

EXAMPLE V

2-Fluorobenzylidene 3-trifluoromethylaniline

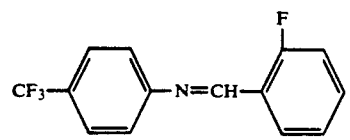

To a toluene (200 mL) solution of 3-aminobenzotrifluoride (10.4 grams, 0.06 mol) was added 2-fluorobenzaldehyde (8.0 grams, 0.06 mol). The mixture was heated under reflux with a Dean-Stark trap for 6 hours. The solvent was removed in a rotary evaporator to give 2-fluorobenzylidene 3-trifluoromethylaniline (16.8 grams, 97% yield, yellow liquid) whose structure was confirmed by nuclear magnetic resonance, infra-red spectroscopy, and mass spectroscopy analysis.

EXAMPLE VI 2,2-Dichloro-3-(2-fluorophenyl)-2-(3-trifluoromethylphenyl)aziridine

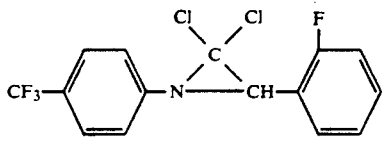

To a methylene chloride (31 mL) solution of the above benzylidene (15.4 grams, 0.06 mol), chloroform (18.6 grams, 0.16 mol) and tetrabutylphosphonium bromide (0.3 grams, catalytic) was added dropwise a 50% aqueous sodium hydroxide solution (30.9 grams, 0.39 mol). The mixture was allowed to stir at room temperature overnight, diluted with more methylene chloride (100 mL) and washed with water (3×30 mL). The solvent was removed in a rotary evaporator. The desired 2,2-Dichloro-3-(2-fluorophenyl)-1-(3-trifluoromethylphenyl)aziridine (19.4 grams, 96% yield) whose structure was confirmed by nuclear magnetic resonance, infra-red spectroscopy and mass spectroscopy analysis.

EXAMPLE VII

N-(3-trifluoromethylphenyl)-2-chloro-2-(2-fluorophenyl)acetamides

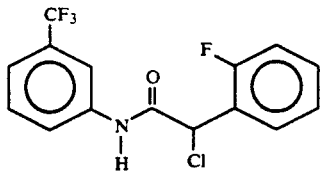

The above aziridine from Example VI (18.1 grams, 0.05 mol) was suspended in water (200 mL) and heated under reflux overnight. The mixture was extracted with ethyl acetate (200 mL), dried with magnesium sulfate. The desired N-(3-trifluoromethylphenyl)-2-chloro-2-(2-fluorophenyl)acetamides (16.6 grams, 100% yield) was obtained whose structure was confirmed by nuclear magnetic resonance, infra-red spectroscopy and mass spectroscopy analysis.

EXAMPLE VIII

N-(3-trifluoromethylphenyl-2-ethylamino-2-(2-fluorophenyl)acetamides

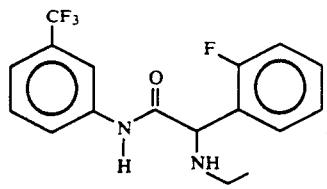

An ethanolic (50 mL) solution of the above N-aryl-2-chloro-2-(substituted phenyl)acetamide (6.0 grams, 0.19 mol), ethyl amine (70% aqueous, 48.5 grams, 0.75 mol) and potassium iodide (2.0 grams, catalytic amount) was allowed to stir at room temperature over the weekend. The reaction was followed by thin layer chromatography (3:1 hexane-ethyl acetate.). The ethanol was removed in a rotary evaporator. To the residue was added ethyl acetate (100 mL) and washed with water (50 mL). The crude product was isolated and purified through conversion to its hydrochloride. Ethanol (100 mL), concentrated hydrochloric acid (10 mL) was added. The hydrochloride salt was dried in the rotary evaporator by azeotropic distillation, washed with ether and resuspended in saturated sodium bicarbonate solution to regenerate the amine. The product was extracted into ethyl acetate and isolated to give the desired N-(3-trifluoromethylphenyl)-2-ethylamino-2-(2-fluorophenyl)acetamide (4.6 grams, 72% yield) whose structure was confirmed by nuclear magnetic resonance, infra-red spectroscopy and mass spectroscopy analysis.

EXAMPLE IX

1-Ethyl-5-(2-fluorophenyl)-3-(3-trifluoromethyl)-phenylimidazolidine-4-one

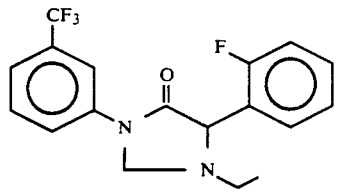

An ethanolic (75 mL) solution of the above N-aryl-2-ethylamino-2-phenylacetamide (2.0 grams, 5.9 mol) and paraformaldehyde (0.18 grams, 5.9 mol) and potassium carbonate (0.41 grams, 2.9 mol) was heated under reflux for 2 hours. The reaction was followed by thin layer chromatography (3:1 hexane-ethyl acetate). The mixture was concentrated in a rotary evaporator. The product was extracted into ethyl acetate and washed with water and isolate to give the desired 1-ethyl-5 -(2-fluorophenyl)-3-(3-trifluoromethylphenyl)imidazolidine-4-one (2.0 grams, 95% yield) whose structure was confirmed by nuclear magnetic resonance, infra-red spectroscopy and mass spectroscopy analysis.

The following is a table of certain selected compounds that were prepared according to the procedures described herein. Compound numbers are assigned to each compound and are used throughout the remainder of the application.

TABLE I

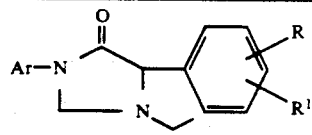

| Cmpd. No. | Ar | R | R¹ | Melting Point |
|---|---|---|---|---|
| 1 | 3-trifluorophenyl | H | H | Oil |
| 2 | 2,5-difluorophenyl | H | H | Oil |
| 3 | 3-trifluoromethylphenyl | 4-Cl | H | Semi-solid |
| 4 | 3-chlorophenyl | H | H | 63-65 |
| 5 | 3-trifluoromethylphenyl | 3-Cl | H | Oil |
| 6 | 3-trifluoromethylphenyl | 2-Br | H | Oil |
| 7 | 3-trifluoromethylphenyl | 4-F | H | 85-90 |
| 8 | 3-trifluoromethylphenyl | 3-CF₃ | H | 75-80 |
| 9 | 3-trifluoromethylphenyl | 2-F | H | Oil |
| 10 | 2-fluorophenyl | 3-CF₃ | H | Oil |
| 11 | 2-fluoro-5-trifluoromethylphenyl | H | H | Oil |
| 12 | 2-fluoro-5-trifluoromethylphenyl | 2-F | H | Oil |
| 13 | 3-trifluoromethylphenyl | 3-Br | H | 83-86 |
| 14 | 3-trifluoromethylphenyl | 4-CH₃ | H | 92-97 |
| 15 | 3-trifluoromethylphenyl | 2-Cl | 4-Cl | Oil |
| 16 | 3-trifluoromethylphenyl | 2-F | 4-F | Oil |
| 17 | 3-trifluoromethylphenyl | 3-CH₃O | H | Oil |
| 18 | 3-trifluoromethylphenyl | 2-Cl | H | Oil |
| 19 | 3-trifluoromethylphenyl | 2-F | 3-F | Oil |
| 20 | 3-trifluoromethylphenyl | 2-CF₃ | H | Oil |
| 21 | 3-trifluoromethylphenyl | 3-NO₂ | H | Oil |
| 22 | 3-trifluoromethylphenyl | 2-F | 5-F | Oil |
| 23 | 3-trifluoromethylphenyl | 3-F | H | 62-67 |
| 24 | 3-trifluoromethylphenyl | 3-F | 4-F | Oil |
| 25 | 3-bromophenyl | 3-NO₂ | H | 89-92 |
| 26 | 3-fluorophenyl | 3-NO₂ | H | Oil |
| 27 | 3-chlorophenyl | 3-NO₂ | H | 96-102 |
| 28 | 3-bromophenyl | H | H | 76-78 |
| 29 | 3-nitrophenyl | H | H | 106-108 |
| 30 | 3-trifluoromethylphenyl | 3-F | 5-F | Oil |

Herbicidal Screening Tests

As previously mentioned, the herein described compounds produced in the above-described manner are phytotoxic compounds which are useful and valuable in controlling various plant species. Selected compounds of this invention were tested a herbicides in the following manner.

Pre-emergence herbicide test

On the day preceding treatment, seeds of seven different weed species are planted in loamy sand soil in individual rows using one species per row across the width of a flat. The seeds used are green foxtail (FT) (*Setaria viridis*), wild oat (WO) (*Avena fatua*), annual moringglory (AMG) (*Ipomoea lacunosa*), velvetleaf (VL) (*Abutilon theophrasti*), Indian mustard (MD) (*Brassica juncea*), and yellow nutsedge (YNS) (*Cyperus esculentus*). Ample seeds are planted to give about 20 to 40 seedlings per row, after emergence, depending upon the size of the plants.

Using a top-loader, 600 milligrams (mg) of the compound to be tested are weighed out into a 60 mL wide-mouth clear bottle and dissolved in 45 mL of acetone. Eighteen mL of this solution are transferred to a 60 mL wide-mouth clear bottle and diluted with 22 mL of a water and acetone mixture (19:1) containing enough polyoxyethylene sorbitan monolaurate emulsifier to give a final solution of 0.5% (v/v). The solution is then sprayed on a seeded flat on a linear spray table calibrated to deliver 80 gallons per acre (748 L/ha). The application rate is 4 lb/acre (4.48 Kg/ha).

After treatment, the flats are placed in the greenhouse at a temperature of 70 to 80° F and watered by sprinkling. Two weeks after treatment, the degree of injury or control is determined by comparison with untreated check plants of the same age. The injury rating from 0 to 100% is recorded for each species as percent control with 0% representing no injury and 100% representing complete control.

The results of the tests as shown in the following Table II.

TABLE II

PRE-EMERGENCE HERBICIDAL ACTIVITY
APPLICATION RATE - 4.48 Kg/ha

| Cmpd. No. | FT | WO | WG | MD | VL | AMG | YNS |
|---|---|---|---|---|---|---|---|
| 1 | 100 | 100 | 100 | 100 | 100 | 100 | 0 |
| 2 | 100 | 70 | 90 | 100 | 85 | 10 | 0 |
| 3 | 100 | 80 | 95 | 100 | 90 | 20 | 0 |
| 4 | 100 | 95 | 100 | 100 | 100 | 20 | 0 |
| 5 | 100 | 95 | 100 | 100 | 100 | 80 | 0 |
| 6 | 100 | 10 | 100 | 100 | 100 | 20 | 0 |
| 7 | 100 | 100 | 100 | 100 | 100 | 75 | 0 |
| 8 | 100 | 85 | 100 | 100 | 100 | 100 | 0 |
| 9 | 100 | 100 | 100 | 100 | 100 | 100 | 20 |
| 10 | 100 | 90 | 100 | 100 | 90 | 30 | 0 |
| 11 | 100 | 100 | 100 | 100 | 100 | 60 | 30 |
| 12 | 100 | 90 | 100 | 100 | 100 | 20 | 0 |
| 13 | 100 | 80 | 100 | 100 | 80 | 40 | 0 |
| 14 | 100 | 30 | 80 | 20 | 10 | 10 | 0 |
| 15 | 0 | 0 | 0 | 0 | 0 | 0 | 0 |
| 16 | 100 | 90 | 100 | 100 | 100 | 100 | 30 |
| 17 | 100 | 50 | 100 | 100 | 100 | 100 | 0 |
| 18 | 100 | 20 | 98 | 100 | 95 | 60 | 0 |
| 19 | 100 | 100 | 100 | 100 | 100 | 100 | 50 |
| 20 | 100 | 0 | 10 | 10 | 0 | 0 | 0 |
| 21 | 100 | 30 | 100 | 100 | 100 | 100 | 0 |
| 22 | 100 | 100 | 100 | 100 | 100 | 100 | 60 |
| 23 | 100 | 95 | 100 | 100 | 100 | 100 | 60 |
| 24 | 100 | 100 | 100 | 100 | 100 | 90 | 0 |
| 25 | 100 | 40 | 80 | 100 | 80 | 70 | 0 |
| 26 | 100 | 80 | 100 | 100 | 100 | 90 | 30 |
| 27 | 100 | 50 | 90 | 100 | 95 | 80 | 0 |
| 28 | 100 | 85 | 100 | 100 | 80 | 40 | 0 |
| 29 | 100 | 30 | 100 | 60 | 0 | 0 | 0 |
| 30 | 100 | 100 | 100 | 100 | 100 | 100 | 30 |

Post-emergence herbicide test

This test was conducted in an identical manner to the testing procedure for the pre-emergence herbicide test, except the seeds of the seven different weed species were planted 10-12 days before treatment. Also, watering of the treated flats was confined to the soil surface and not to the foliage of the sprouted plants.

The result of the post-emergence herbicide test are reported in Table III.

TABLE III

POST-EMERGENCE HERBICIDAL ACTIVITY
APPLICATION RATE - 4.48 Kg/ha

| Cmpd. No. | FT | WO | WG | MD | VL | AMG | YNS |
|---|---|---|---|---|---|---|---|
| 1 | 90 | 80 | 85 | 80 | 80 | 30 | 0 |
| 2 | 100 | 30 | 30 | 100 | 100 | 10 | 0 |
| 3 | 100 | 60 | 80 | 100 | 90 | 20 | 0 |
| 4 | 100 | 80 | 85 | 100 | 100 | 75 | 40 |
| 5 | 100 | 85 | 100 | 100 | 80 | 80 | 30 |
| 6 | 100 | 5 | 95 | 100 | 100 | 60 | 0 |
| 7 | 100 | 100 | 100 | 100 | 100 | 60 | 30 |
| 8 | 100 | 80 | 80 | 100 | 90 | 60 | 0 |
| 9 | 100 | 100 | 90 | 100 | 90 | 75 | 70 |
| 10 | 20 | 20 | 20 | 100 | 20 | 20 | 0 |
| 11 | 100 | 100 | 100 | 100 | 100 | 60 | 20 |

TABLE III-continued
POST-EMERGENCE HERBICIDAL ACTIVITY
APPLICATION RATE - 4.48 Kg/ha

| Cmpd. No. | FT | WO | WG | MD | VL | AMG | YNS |
|---|---|---|---|---|---|---|---|
| 12 | 100 | 100 | 80 | 100 | 80 | 60 | 30 |
| 13 | 100 | 20 | 100 | 100 | 100 | 60 | 0 |
| 14 | 20 | 0 | 20 | 100 | 60 | 0 | 0 |
| 15 | 0 | 0 | 0 | 0 | 0 | 0 | 0 |
| 16 | 100 | 85 | 100 | 100 | 100 | 100 | 50 |
| 17 | 100 | 20 | 40 | 100 | 100 | 20 | 0 |
| 18 | 100 | 60 | 90 | 100 | 80 | 20 | 0 |
| 19 | 100 | 100 | 100 | 100 | 100 | 80 | 80 |
| 20 | 0 | 0 | 0 | 80 | 20 | 10 | 0 |
| 21 | 100 | 50 | 50 | 100 | 90 | 80 | 0 |
| 22 | 100 | 80 | 80 | 100 | 90 | 80 | 50 |
| 23 | 100 | 80 | 80 | 80 | 90 | 80 | 70 |
| 24 | 100 | 80 | 80 | 100 | 90 | 100 | 80 |
| 25 | 30 | 30 | 30 | 90 | 80 | 80 | 0 |
| 26 | 80 | 60 | 60 | 80 | 80 | 80 | 60 |
| 27 | 30 | 50 | 50 | 90 | 80 | 80 | 30 |
| 28 | 30 | 30 | 30 | 100 | 30 | 10 | 0 |
| 29 | 0 | 0 | 20 | 20 | 0 | 0 | 0 |
| 30 | 80 | 80 | 80 | 80 | 80 | 80 | 70 |

The compounds of the present invention and their salts are useful as herbicides and can be applied in a variety of ways at various concentrations. In practice, the compounds or salts are formulated into herbicidal compositions, by admixture, in herbicidally effective amounts, with the adjuvants and carriers normally employed for facilitating the dispersion of active ingredients for agricultural applications, recognizing the fact that the formulation and mode of application of a toxicant may affect the activity of the materials in a given application. Thus, these active herbicidal compounds or salts can be formulated as granules of relatively large particle size, as wettable powders, as emulsifiable concentrates, as powdery dusts, as flowables, as solutions or as any of several other known types of formulations, depending upon the desired mode of application. These formulations may contain as little as about 0.5% to as much as about 95% or more by weight of active ingredient. A herbicidally effective amount depends upon the nature of the seeds or plants to be controlled and the rate of application varies from about 0.01 to approximately 10 pounds per acre, preferably from about 0.02 to about 4 pounds per acre.

Wettable powders are in the form of finely divided particles which disperse readily in water or other dispersants. The wettable powder is ultimately applied to the soil either as a dry dust or as a dispersion in water or other liquid. Typical carriers for wettable powders include fuller's earth, kaolin clays, silicas and other readily wettable organic or inorganic diluents. Wettable powders normally are prepared to contain about 5% to about 95% of the active ingredient and usually also contain a small amount of wetting, dispersing, or emulsifying agent to facilitate wetting and dispersion.

Emulsifiable concentrates are homogeneous liquid compositions which are dispersible in water or other dispersant, and may consist entirely of the active compound or salt with a liquid or solid emulsifying agent, or may also contain a liquid carrier, such as xylene, heavy aromatic naphtha, isophorone and other non-volatile organic solvents. For herbicidal application, these concentrates are dispersed in water or other liquid carrier and normally applied as a spray to the area to be treated. The percentage by weight of the essential active ingredient may vary according to the manner in which the composition is to be applied, but in general comprises about 0.5% to 95% of active ingredient by weight of the herbicidal composition.

Granular formulations wherein the toxicant is carried on relatively coarse particles, are usually applied without dilution to the area in which suppression of vegetation is desired. Typical carriers for granular formulations include sand, fuller's earth, attapulgite clay, bentonite clays, montmorillonite clay, vermiculite, perlite and other organic or inorganic materials which absorb or which may be coated with the toxicant. Granular formulations normally are prepared to contain from about 1% to about 25% of active ingredients which may include surface-active agents such as heavy aromatic naphtha, kerosene or other petroleum fractions, or vegetable oils; and/or stickers such as destrins, glue or synthetic resins.

Typical wetting, dispersing or emulsifying agents used in agricultural formulations include, for example, the alkyl and alkylaryl sulfonates and sulfates and their salts; polyhydric alcohols; polyethoxylated alcohols; esters and fatty amines; and other types of surface-active agents, many of which are available in commerce. The surface-active agent, when used, normally comprises from 0.1% to 15% by weight of the herbicidal composition.

Dusts, which are free-flowing admixtures of the active ingredients with finely divided solids such as talc, clays, flours and other organic and inorganic solids which act as dispersants and carriers for the toxicant, are useful formulations for soil-incorporating application.

Pastes, which are homogeneous suspensions of a finely divided solid toxicant in a liquid carrier such as water or oil, are employed for specific purposes. These formulations normally contain about 5% to about 95% of active ingredient by weight, and may also contain small amounts of a wetting, dispersing or emulsifying agent to facilitate dispersion. For application, the pastes are normally diluted and applied as a spray to the area to be affected.

Other useful formulations for herbicidal applications include simple solutions of the active ingredient in a dispersant in which it is completely soluble at the desired concentration, such as acetone, alkylated naphthalenes, xylene and other organic solvents. Pressurized sprays, typically aerosols, wherein the active ingredient is dispersed in finely-divided form as a result of vaporization of a low boiling dispersant solvent carrier, such as the Freons, may also be used.

The phytotoxic compositions of this invention can be applied to the plants in any conventional manner. Thus, the dust and liquid compositions can be applied to the plant by the use of power dusters, boom and hand sprayers and spray dusters. The compositions can also be applied from airplanes as a dust or a spray or by rope wick applications because they are effective in very low dosages. In order to modify or control growth of germinating seeds or emerging seedlings, as a typical example, the dust and liquid compositions can be applied to the soil according to conventional methods and can be distributed in the soil to a depth of at least ½ inch below the soil surface. It is not necessary that the phytotoxic compositions be mechanically admixed with the soil particles since these compositions can also be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging, or mixing operations. In the following examples the herbicidal compound can be substituted with the herbicidal salt of the compound.

| General Formula with Ranges | | Specific Formula | |
|---|---|---|---|
| EMULSIFIABLE CONCENTRATE FORMULATIONS | | | |
| herbicidal compound | 5–55 | herbicidal compound | 24 |
| surfactant(s) | 5–25 | proprietary blend of oil- | 10 |
| solvent(s) | 20–90 | soluble sulfonates and | |
| | 100% | polyoxyethylene ethers | |
| | | polar solvent | 27 |
| | | petroleum hydrocarbon | 39 |
| | | | 100% |
| WETTABLE POWDER FORMULATIONS | | | |
| herbicidal compound | 3–90 | herbicidal compound | 80 |
| wetting agent | 0.5–2 | sodium dialkyl naphthalene | 0.5 |
| dispersing agent | 1–8 | sulfonate | |
| diluent(s) | 8.5–85.5 | sodium lignosulfonate | 7 |
| | 100% | attapulgite clay | 12.5 |
| | | | 100% |
| EXTRUDED GRANULAR FORMULATIONS | | | |
| herbicidal compound | 1–20 | herbicidal compound | 10 |
| binding agent | 0–10 | lignin sulfonate | 5 |
| diluent(s) | 70–99 | calcium carbonate | 85 |
| | 100% | | 100% |
| FLOWABLE FORMULATIONS | | | |
| herbicidal compound | 20–70 | herbicidal compound | 45 |
| surfactant(s) | 1–10 | polyoxyethylene ether | 5 |
| suspending agent(s) | 0.05–1 | attagel | 0.05 |
| antifreeze agent | 1–10 | propylene glycol | 10 |
| antimicrobial agent | 1–10 | 1,2-benzisothiazoline-3- | 0.03 |
| antifoam agent | 0.1–1 | one | |
| solvent | 7.95–76.85 | silicone defoamer | 0.02 |
| | 100% | water | 39.9 |
| | | | 100% |

When salts are used as the active ingredient in the herbicidal compositions of this invention it is recommended to use salts that are agriculturally acceptable.

The phytotoxic compositions of this invention can also contain other additives, for example, fertilizers, other herbicides and other pesticides, used as adjuvant or in combination with any of the above-described adjuvants. Fertilizers useful in combination with the active ingredients include, for example, ammonium nitrate, urea and superphosphate.

The herbicidal compounds of this invention can be used in combination with other herbicidal compounds for broader spectrum control of undesirable vegetation. Examples of other herbicidal compounds are as follows:

1. ANILIDES

Alachlor—2-chloro-2',6'-diethyl-N-(methoxymethyl) acetanilide
Metolachlor—2-chloro-N-(2-ethyl-6-methylphenyl)-N-(2-methoxy-1-methylethyl)acetamide
Propanil—N-(3,4-dichlorophenyl)propionanilide

2. TRIAZINES

Atrazine—2-chloro-4-(ethylamino)-6-isopropylamino)-s-triazine
Cyanazine—2-chloro-4-(1-cyano-1-methylethylamino)-6-ethylamino-s-triazine
Metribuzin—4-amino-6-tert-butyl-3-(methylthio)-1,2,4-triazin-5(4H)-one

3. THIOCARBAMATES

Molinate—S-ethyl hexahydro-1H-azepine-1-carbothioate
Butylate—S-ethyl diisobutylthiocarbamate

4. UREAS

Monuron—3-(p-chlorophenyl)-1,1-dimethylurea
Linuron—3-(3,4-dichlorophenyl)-1-methoxy-1-methylurea

5. TOLUIDINES

Trifluralin—α,α,α-trifluoro-2,6-dinitro-N,N-dipropyl-p-toluidine
Pendimethalin—N-(1-ethylpropyl)-3,4-dimethyl-2,6-dinitrobenzeneamine

6. HORMONES 2,4-D—(2,4-dichlorophnoexy) acetic acid
MCPA—(2-methyl-4-chlorophenoxy) acetic acid

7. DIAZINES

Bentazon—3-isopropyl-1H-2,3,1-benzothiadiazin-4(3H)-one 2,2-dioxide
Oxadiazon—2-tert-butyl-4-(2,4-dichloro-5-isopropoxyphenyl)- $\Delta^2$-1,3,4-oxadiazolin-5-one

8. DIPHENYL ETHERS

Acifluorfen—sodium 5-[2-chloro-4-(trifluoromethyl)-phenoxy]-2-nitrobenzoate
Fluazifop-butyl —(±)-butyl 2-[4[(5-(trifluoromethyl)-2-pyridinyl)oxy]phenoxy]propanoate
Chlomethoxynil—2,4-dichlorophenyl 3-methoxy-4-nitrophenyl ether

9. IMIDAZOLINONES

Imazaquin—2-[4,5-dihydro-4-methyl-4-(I-methylethyl)-5-oxo-1H-imidazol-2-yl]-3-quinolin carboxylic acid

10. SULFONYL UREAS

Bensulfuron methyl—methyl 2-[[[[[(4,6-dimethoxypyrimidin-2-yl)amino]carbonyl]amino]sulfonyl]methyl]benzoate Chlorimuron ethyl—ethyl 2-(((((4-chloro-6-methoxypyromidin-2-yl)amino)carbonyl)amino)sulfonyl)benzoate

11. MISCELLANEOUS COMPOUNDS

Dimethazone—2-(2-chlorophenyl)methyl-4,4-dimethyl-3-isoxazolidinone

Norflurazon—4-chloro-5-(methylamino)-2-α,α,α-trifluoro-m-tolyl)3-(2H)-pyridazinone Dalapon—2,2-dichloropropionic acid Glyphosate—isopropyl amine salt of N-(phosphonomethyl) glycine Fenoxaprop-ethyl—(+)-ethyl-2,4-((6-chloro-2-benzoxazoly loxy)phenoxy)propanoate

What is claimed is:

1. Compounds of the formula

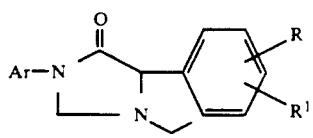

wherein

R is hydrogen; halogen, trifluoromethyl or $C_1$-$C_4$ alkoxy, $R_1$ is hydrogen; halogen, trifluoromethyl or $C_1$-$C_4$ alkoxy, Ar is the group

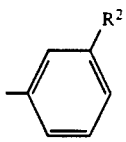

wherein $R^2$ is trifluoromethyl or halogen, or the group

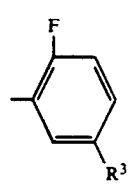

wherein $R^3$ is hydrogen, fluorine or trifluoromethyl.

2. The compounds of claim 1 wherein
R is fluorine or chlorine
$R^4$ is hydrogen or fluorine
Ar is the group

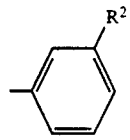

$R^2$ is trifluoromethyl.

3. The compounds of claim 1 wherein
R is hydrogen or fluorine
$R^1$ is hydrogen
Ar is the group

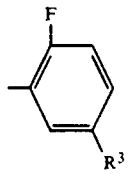

wherein $R^3$ is trifluoromethyl.

4. The compounds of claim 1 wherein
R is 3—chlorine
$R^1$ is hydrogen
Ar is the group

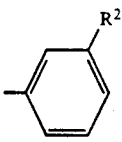

wherein $R^2$ is trifluoromethyl.

5. The compounds of claim 1 wherein
R is 2-fluorine or 4-fluorine
$R^1$ is hydrogen
Ar is the group wherein $R^2$ is trifluoromethyl.

6. The compounds of claim 1 wherein
R is 2-fluorine
$R^1$ is 3-fluorine, 4-fluorine or 5-fluorine
Ar is the group

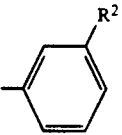

wherein $R^2$ is trifluoromethyl.

7. The compounds of claim 1 wherein
R is 3-chlorine
$R^1$ is hydrogen
Ar is the group

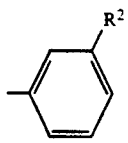

wherein R² is trifluoromethyl.
8. The compounds of claim 1 wherein
R is hydrogen or 2-fluorine
R¹ is hydrogen
Ar is the group

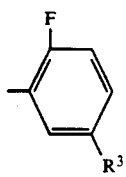

wherein R³ is trifluoromethyl.
9. A herbicidal composition comprising an herbicidally active compound of the formula

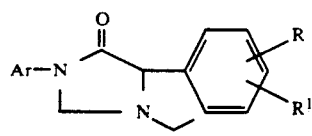

wherein
R is hydrogen; halogen, trifluoromethyl or C₁-C₄ alkoxy,
R₁ is hydrogen, halogen, trifluormethyl or C₁-C₄ alkoxy,
Ar is the group

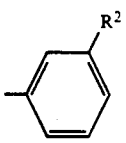

wherein R² is trifluoromethyl or halogen, or the group

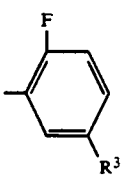

wherein R³ is hydrogen, fluorine or trifluormethyl and an inert carrier therefor.
10. The herbicidal composition of claim 9 wherein
R is hydrogen or fluorine
R⁴ is hydrogen or fluorine
Ar is the group

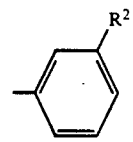

R² is trifluoromethyl.
11. The herbicidal composition of claim 9 wherein
R is hydrogen or fluorine
R¹ is hydrogen
Ar is the group

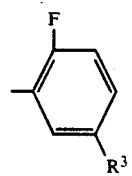

wherein R³ is trifluoromethyl.
12. The herbicidal composition of claim 9 wherein
R is 3—chlorine
R¹ is hydrogen
Ar is the group

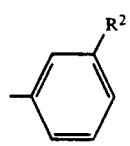

wherein R² is trifluoromethyl.
13. The herbicidal composition of claim 9 wherein
R is 2-fluorine or 4-fluorine
R¹ is hydrogen
Ar is the group

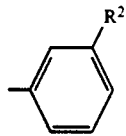

wherein R² is trifluoromethyl.
14. The herbicidal composition of claim 9 wherein
R is 2-fluorine
R¹ is 3-fluorine, 4-fluorine or 5-fluorine
Ar is the group

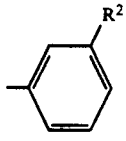

wherein R² is trifluoromethyl.
15. The herbicidal composition of claim 9 wherein
R is 3-chlorine
R¹ is hydrogen
Ar is the group

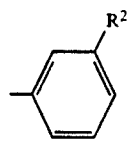

wherein R² is trifluoromethyl.

16. The herbicidal composition of claim 9 wherein
R is hydrogen or 2-fluorine
R¹ is hydrogen
Ar is the group

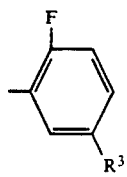

wherein R³ is trifluoromethyl.

17. A method of controlling undesirable vegetation comprising applying to the area where control is desired, an herbicidally effective amount of a compound having the formula

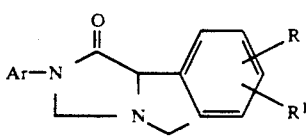

wherein
R is hydrogen; halogen, trifluoromethyl or $C_1$-$C_4$ alkoxy,
$R_1$ is hydrogen; halogen, trifluoromethyl or $C_1$-$C_4$ alkoxy,
Ar is the group

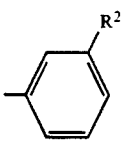

wherein R² is trifluoromethyl or halogen, or the group

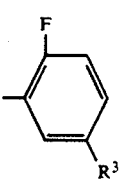

wherein R³ is hydrogen, fluorine or trifluoromethyl.
18. The method of claim 17 wherein
R is fluorine or chlorine
R⁴ is hydrogen or fluorine
Ar is the group

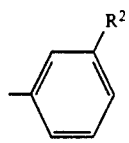

wherein R² is trifluoromethyl.
19. The method of claim 17 wherein
R is hydrogen or fluorine
R¹ is hydrogen
Ar is the group

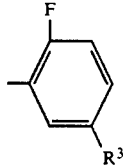

wherein R³ is trifluoromethyl.
20. The method of claim 17 wherein
R is 3—chlorine
R¹ is hydrogen
Ar is the group

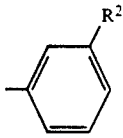

wherein R² is trifluoromethyl.
21. The method of claim 17 wherein
R is 2-fluorine or 4-fluorine
R¹ is hydrogen
Ar is the group

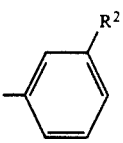

wherein R² is trifluoromethyl.
22. The method of claim 17 wherein
R is 2-fluorine
R¹ is 3-fluorine, 4-fluorine or 5-fluorine
Ar is the group

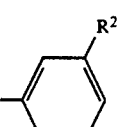

wherein R² is trifluoromethyl.
23. The method of claim 17 wherein
R is 3-chlorine
R¹ is hydrogen
Ar is the group

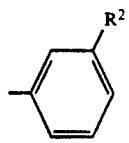
wherein R² is trifluoromethyl.
24. The method of claim 17 wherein
R is hydrogen or 2-fluorine
R¹ is hydrogen
Ar is the group
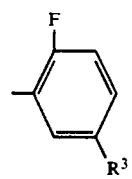
wherein R³ is trifluoromethyl.
* * * * *